(12) United States Patent
Francke et al.

(10) Patent No.: US 7,099,436 B2
(45) Date of Patent: Aug. 29, 2006

(54) COHERENT SCATTER IMAGING

(75) Inventors: Tom Francke, Sollentuna (SE);
Christer Ullberg, Sollentuna (SE)

(73) Assignee: XCounterAB, Danderyd (SE)

( * ) Notice: Subject to any disclaimer, the term of this patent is extended or adjusted under 35 U.S.C. 154(b) by 29 days.

(21) Appl. No.: 10/726,694

(22) Filed: Dec. 4, 2003

(65) Prior Publication Data

US 2005/0094767 A1 May 5, 2005

(30) Foreign Application Priority Data

Nov. 3, 2003 (SE) .................................... 0302900

(51) Int. Cl.
*G01N 23/04* (2006.01)
*G01T 1/16* (2006.01)
(52) U.S. Cl. .................. 378/62; 378/87; 250/385.1
(58) Field of Classification Search .............. 378/86, 378/87, 37, 62; 250/374, 385.1
See application file for complete search history.

(56) References Cited

U.S. PATENT DOCUMENTS

| | | | |
|---|---|---|---|
| 3,936,639 A | 2/1976 | Barrett |
| 4,896,342 A | 1/1990 | Harding |
| 4,899,283 A | 2/1990 | Annis |
| 6,118,125 A | 9/2000 | Francke et al. |
| 6,175,117 B1 | 1/2001 | Komardin et al. |
| 6,337,482 B1 | 1/2002 | Francke |
| 6,373,065 B1 | 4/2002 | Francke et al. |
| 6,385,282 B1 | 5/2002 | Francke et al. |
| 6,414,317 B1 | 7/2002 | Francke et al. |
| 6,442,233 B1 | 8/2002 | Grodzins et al. |
| 6,476,397 B1 | 11/2002 | Francke et al. |
| 6,477,223 B1 | 11/2002 | Francke |
| 6,518,578 B1 | 2/2003 | Francke et al. |
| 6,522,722 B1 | 2/2003 | Francke |
| 6,546,070 B1 | 4/2003 | Francke |
| 6,556,650 B1 | 4/2003 | Francke |
| 6,600,804 B1 | 7/2003 | Francke et al. |
| 6,627,897 B1 | 9/2003 | Francke et al. |
| 2002/0150202 A1 | 10/2002 | Harding et al. |

FOREIGN PATENT DOCUMENTS

| | | |
|---|---|---|
| DE | 38 19 739 A1 | 12/1989 |
| EP | 0354045 | 2/1990 |
| EP | 1062914 | 12/2000 |
| JP | 5-146426 | 6/1993 |
| WO | WO 03069371 | 8/2003 |

OTHER PUBLICATIONS

Search Report for International Application No. PCT/SE03/00829.
Jens-Peter Schlomka, et al. "Coherent Scatter Computed Tomography—A Novel Medical Imaging Technique", Medical Imaging 2003.
Written Opinion for PCT/SE2004/001558 (Dec. 13, 2005).

*Primary Examiner*—Edward J. Glick
*Assistant Examiner*—Chih-Cheng Glen Kao
(74) *Attorney, Agent, or Firm*—Harness, Dickey & Pierce

(57) ABSTRACT

A method for the detection of ionizing radiation including directing ionizing radiation towards an object to be examined, preventing Compton scattered radiation from being detected, and detecting ionizing radiation spatially resolved as transmitted through the object to reveal a spatially resolved density of the object. The ionizing radiation is provided within a spectral range such that more photons of the ionizing radiation are Compton scattered than absorbed through the photoelectric effect in the object, thereby reducing the radiation dose to the to the object.

16 Claims, 4 Drawing Sheets

COHERENT SCATTER IMAGING

FIELD OF THE INVENTION

The invention relates generally to apparatuses and methods for obtaining coherent scatter imaging data of an examination object.

BACKGROUND OF THE INVENTION AND RELATED ART

An X-ray medical diagnostic method such as mammography is a low-dose procedure that creates one or more images of a part of a patient such as a breast thereof, which is to be examined, e.g. for detection of early stages of cancer.

The mammography diagnostic procedure generally includes obtaining two images of each of the patient's breasts, one from above and one from the side. A physician or radiologist then reviews the images of the breast, i.e., mammograms, to identify any breast cancer.

While this procedure is one of the best methods of detecting early forms of breast cancer, it is still possible for the detection of breast cancer to be missed by a physician or radiologist reviewing the mammograms. For example, breast cancer may be missed by being obscured by radiographically dense, fibroglandular breast tissue.

Coherent scatter imaging has been studied in an effort to detect early forms of breast cancer, see e.g. Coherent Scatter Computed Tomography—A Novel Medical Imaging technique, J.-P. Schlomka, A. Harding, U. van Stevendaal, M. Grass, and G. Harding, Medical Imaging 2003: Physics of Medical Imaging, M. J. Yaffe and L. E. Antonuk, Editors, Proceedings of SPIE, Vol. 5030, 2003, p. 256.

The method is derived from ART methods described in the literature and is based on a back-projection step using data from measurement of the angular spread distribution of photons as scattered from an illuminated slice within the object to be examined.

SUMMARY OF THE INVENTION

However, the method disclosed by J.-P. Schlomka et al. suffers from a limited spatial resolution. Each individual signal is collected along the complete length of the area of interaction between the incident radiation beam and the examination object, i.e. along the complete of the trajectory of the radiation photons of the radiation beam within the object. The experimental setup includes certainly a collimator made of thin tungsten lamellae placed in front of the detector, but these lamellae are only there to provide for an image with low spatial resolution; a 2D detector was modeled by a single 1D vertical detector column based on GSO crystals and photomultipliers.

A main object of the invention is therefore to provide apparatuses and methods, respectively, for providing coherent scatter imaging data with a better spatial resolution than what is obtainable by using the above-identified prior art method.

In this respect there is a particular object to provide such apparatuses and methods, which provide coherent scatter imaging data, by which high-quality one-, two-, and even three-dimensional images with high spatial resolution, scattering angular resolution, signal-to-noise ratio, dynamic range, and image contrast can be produced.

A still further object of the invention is to provide such apparatuses and methods, which provide conventional transmission imaging data simultaneously with the coherent scatter imaging data.

A yet further object of the invention is to provide such apparatuses and methods, which are reliable, accurate, uncomplicated and inexpensive.

These objects, among others, are attained by apparatuses and methods as claimed in the appended claims.

In order for the invention to operate properly, unwanted scattered radiation has to be discriminated from being detected to a particularly large extent. The line detectors, on which the present invention are based, have each an elongated opening for entry of a respective fan-shaped coherently scattered ray bundle; a row of individual elongated detector elements arranged essentially parallel with the elongated opening; and is of the kind wherein charges or photons generated by interactions between the respective fan-shaped coherently scattered ray bundle and a detection medium within the line detector and traveling in a direction essentially perpendicular to the respective fan-shaped coherently scattered ray bundle, are detected by the row of individual detector elements. Such edge-on detectors can be made extremely direction sensitive.

Preferably, but not exclusively, the line detector units are each a gaseous-based parallel plate detector, especially a detector wherein avalanche amplification is performed to amplify the signals, comprising substantial planar cathode and combined anode/readout arrangements.

According to one aspect of the present invention an apparatus for obtaining coherent scatter imaging data of an examination object is provided, the apparatus comprising a radiation source arrangement for creating a radiation beam of ionizing radiation centered around an axis of symmetry, which radiation beam is directed through the examination object; and a radiation detector arrangement comprising a stack of line detector units, each being directed towards a small portion of a trajectory of the radiation beam in the examination object to allow a substantially fan-shaped ray bundle of the radiation beam as coherently scattered in the examination object to enter the line detector unit and be detected therein. Each of the line detector units is of the kind described above. The line detector units and their respective individual detector elements are formed and oriented so as to allow simultaneous recording of coherent scatter imaging data sufficient to form a plurality of one-dimensional images, each being composed of radiation as coherently scattered in the examination object in a respective angle.

Preferably, the line detector units are directed towards different positions along the trajectory of the radiation beam in the examination object to allow different fan-shaped ray bundles of the radiation beam as coherently scattered in different small portions of the examination object to enter the line detector units and be detected therein. Hereby, a signal from each of the line detector units is needed to form one of the plurality of one-dimensional images.

Still preferably, the row of detector elements of each of the line detector units is essentially orthogonal to a plane, in which the axis of symmetry and the stack of line detector units are located; and the detector elements of each of the line detector units are separated, elongated and directed so their extension lines converge in a respective point in said different small portions, and detect therefore different angular portions of the fan-shaped ray bundle entered into the respective line detector unit. Hereby, a signal from each of the line detector unit is needed to form each of the plurality of one-dimensional images.

In an alternative version of the invention, the radiation beam of ionizing radiation has a substantially line-shaped cross-section; the openings of the line detector units are parallel with the substantially line-shaped cross-section of the radiation beam; the line detector units are directed towards a single small portion of the trajectory of the radiation beam in the examination object; and the detector elements of each of the line detector units are separated, elongated and arranged to provide coherent scatter imaging data sufficient to form one of the plurality of one-dimensional images.

According to another aspect of the present invention a method for obtaining coherent scatter imaging data of an examination object is provided, the method comprising the steps of (i) directing a radiation beam of ionizing radiation centered around an axis of symmetry through the examination object; (ii) directing each one of a plurality of line detector units arranged in a stack towards a small portion of the trajectory of the radiation beam in the examination object to allow a substantially fan-shaped ray bundle of the radiation beam as coherently scattered in the examination object to enter the line detector unit; and (iii) detecting the fan-shaped ray bundle entered into the line detector units. Each of the line detector units is of the kind described above. The line detector units and their respective individual detector elements are formed and oriented so as to allow simultaneous recording of coherent scatter imaging data sufficient to form a plurality of one-dimensional images, each being composed of radiation as coherently scattered in the examination object in a respective angle.

Preferably, the method comprises to use a detection arrangement, wherein the line detector units are directed towards different positions along the trajectory of the radiation beam in the examination object to allow different fan-shaped ray bundles of the radiation beam as coherently scattered in different small portions of the examination object to enter the line detector units and be detected therein; the row of detector elements of each of the line detector units is essentially orthogonal to a plane, in which the axis of symmetry and the stack of line detector units are located; and the detector elements of each of the line detector units are separated, elongated and directed so their extension lines converge in a respective point in said small portions, and detect therefore different angular portions of the fan-shaped ray bundle entered into the respective line detector unit.

According to yet another aspect of the present invention an apparatus for obtaining coherent scatter imaging data of an examination object is provided, the apparatus comprising a radiation source arrangement for creating a collimated radiation beam of ionizing radiation centered around an axis of symmetry, which radiation beam is directed through the examination object; and a line detector unit being directed towards a small portion of a trajectory of the radiation beam in the examination object to allow a substantially fan-shaped ray bundle of the radiation beam as coherently scattered in the examination object to enter the line detector unit and be detected therein. The line detector unit detector is of the kind described above, the row of detector elements of the line detector unit is essentially orthogonal to the axis of symmetry; and the detector elements of the line detector unit are separated, elongated and directed so their extension lines converge in a single point in the small portion, and detect therefore different angular portions of the fan-shaped ray bundle entered into the line detector unit.

Further characteristics of the invention, and advantages thereof, will be evident from the detailed description of preferred embodiments of the present invention given hereinafter and the accompanying FIGS. 1–3, which are given by way of illustration only, and thus are not limitative of the present invention.

BRIEF DESCRIPTION OF THE DRAWINGS

Identical reference numerals are used throughout the Figures to denote identical or similar components, portions, details and the like of the various embodiments.

DESCRIPTION OF PREFERRED EMBODIMENTS

Figure 1:
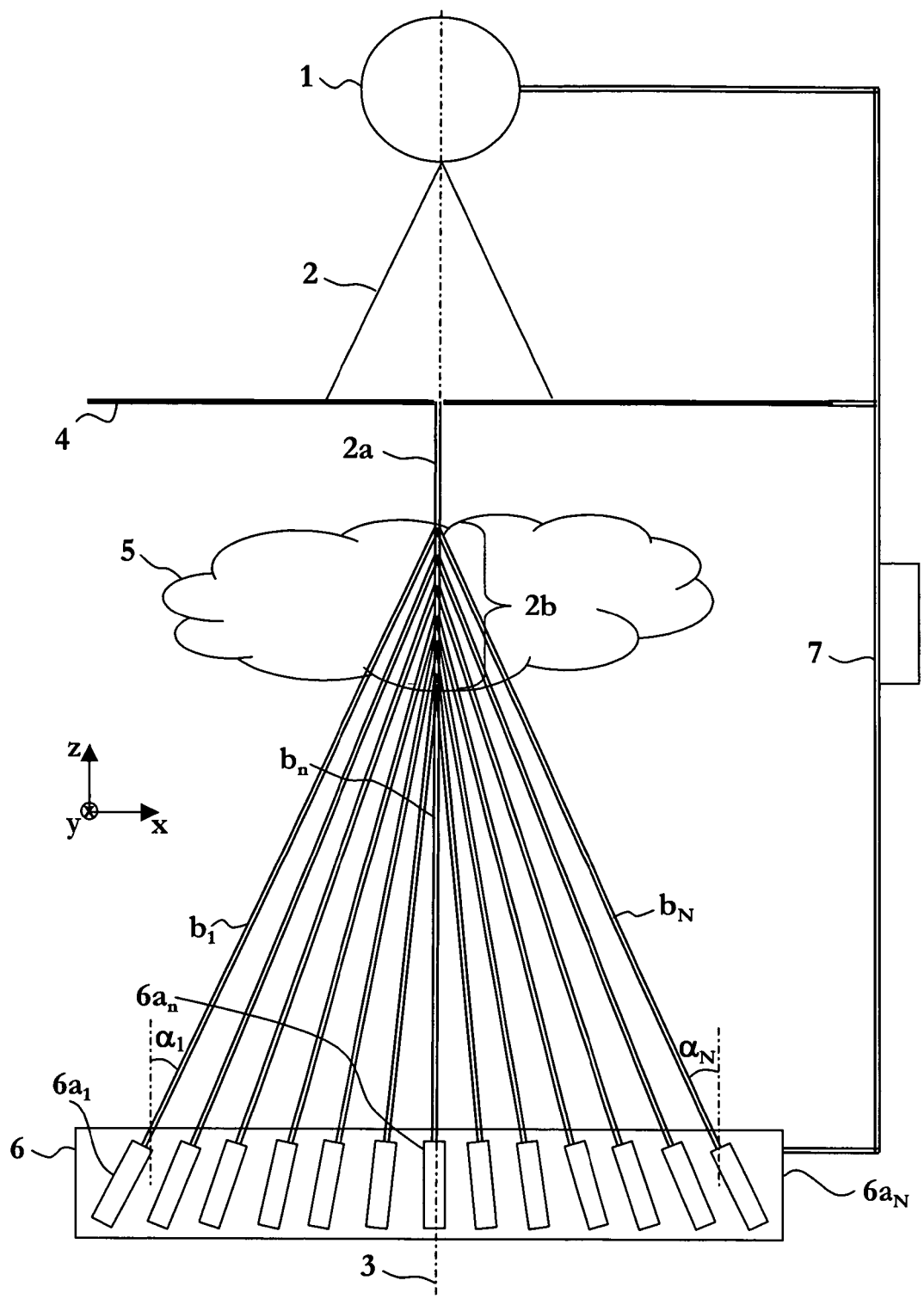
FIG. 1 illustrates schematically, in a side view, an apparatus for obtaining coherent scatter imaging data for x-ray examination of an object according to a preferred embodiment of the present invention.

The apparatus of FIG. 1 comprises a divergent X-ray source 1, which produces X-rays 2 centered around an axis of symmetry 3; an aperture collimator 4 having a circular opening for collimating the emitted X-rays 2 to form a well defined collimated radiation beam 2a; a radiation detector arrangement 6; and a device 7 for rigidly connecting the X-ray source 1, the collimator 4, and the radiation detector arrangement 6 to each other and moving the X-ray source 1, the collimator 4, and the radiation detector arrangement 6 relative an object 5, which is to be examined, to scan the object 5. Alternatively, the X-ray source 1, the collimator 4, and the radiation detector arrangement 6 are held still and the object 5 is moved during the scanning.

The radiation detector arrangement 6 comprises a row or stack of one-dimensional or line detectors $6a_1$–$6a_{n-1}$, $6a_{n+1}$–$6a_N$ directed towards different positions of the trajectory $2b$ of the radiation beam $2a$ in the examination object 5 to allow different fan-shaped ray bundles b1, . . . , $b_{n-1}$, $b_{n+1}$ . . . , $b_N$ of the radiation beam $2a$ as coherently scattered in different small portions of the examination object 5 along the trajectory $2b$ to enter the line detectors and be detected therein. The line detectors $6a_1$–$6a_{n-1}$, $6a_{n+1}$–$6a_N$ are preferably directed towards the different positions along the trajectory $2b$ of the radiation beam $2a$ in the object 5, which directions define angles $\alpha_1, \ldots, \alpha_{n-1}, \alpha_{n+1}, \ldots \alpha_N$ with respect to the axis of symmetry 3 in the xz-plane, in which the axis of symmetry 3 and the row or stack of line detectors $6a_1$–$6a_{n-1}$, $6a_{n+1}$–$6a_N$ exist, which angles $\alpha_1, \ldots, \alpha_{n-1}, \alpha_{n+1}, \ldots \alpha_N$ have the same magnitude.

Figure 2A:
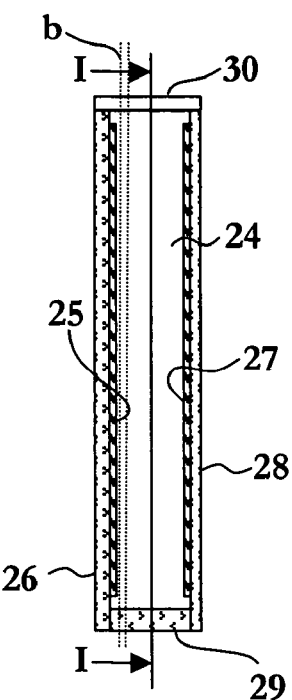
FIG. 2a illustrates schematically, in a cross-sectional side view, a line detector comprised in the apparatus of FIG. 1.
Figure 2B:
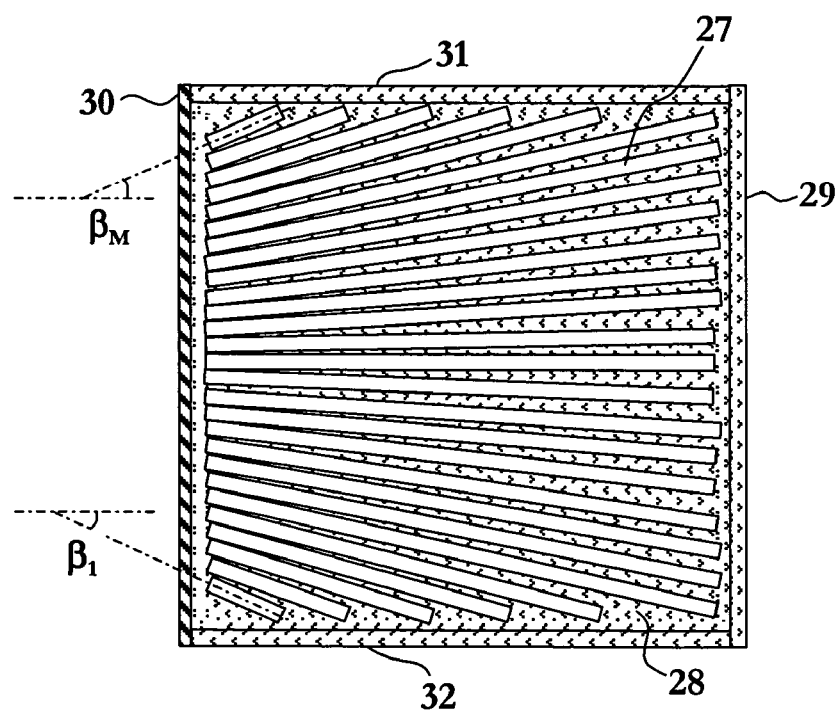
FIG. 2b illustrates schematically a cross-sectional view of the detector of FIG. 2a along the line I —I.

One of the line detectors $6a_1$–$6a_{n-1}$, $6a_{n+1}$–$6a_N$ is illustrated more in detail in FIGS. 2a–b. The line detector has an elongated opening 30 for entry of the fan-shaped coherently scattered ray bundle; a row of elongated individual detector elements or strips 27 arranged essentially parallel with the elongated opening 30; and is of the kind wherein charges or photons generated by interactions between the fan-shaped coherently scattered ray bundle entered into the detector and a detection medium 24 within the line detector and traveling in a direction essentially perpendicular to the fan-shaped coherently scattered ray bundle, can be detected by the row of individual detector elements 27.

Preferably, the line detector is a gaseous-based parallel plate detector, especially a detector wherein avalanche amplification is performed to amplify the signals, comprising substantial planar cathode 25, 26 and combined anode/readout 27, 28 arrangements. Each of the electrode arrangements 25, 26; 27, 28 includes an electrically conducting electrode layer 25, 27 supported by a respective dielectric substrate 26, 28, wherein the arrangements are oriented so that the conductive cathode 25 and anode 27 layers are facing each other.

Preferably, the dielectric substrates 26, 28 and the window 30 define together with sidewalls 29, 31, 32 a gas-tight confinement capable of being filled with an ionizable gas or gas mixture. Alternatively, the electrode arrangements are arranged within an external gas-tight casing (not illustrated). The ionizable gas or gas mixture may e.g. comprise krypton and carbon dioxide or xenon and carbon dioxide.

Such gaseous-based parallel plate detector has been found to be capable to be made extremely direction sensitive, and thus very suitable for use in applications where unwanted scattered radiation has to be strongly attenuated. In fact the view of field of the gaseous-based parallel plate detector, schematically indicated by b in FIG. 2a, is extremely thin—much thinner than the width of the window 30 and thinner than a typical thickness of the fan-shaped coherently scattered ray bundle entered into the detector. The discovery of this property was an absolute prerequisite for inventing an apparatus for high-energy radiographic measurement of an object, which prevents Compton scattered radiation from being detected, see our pending U.S. patent application Ser. No. 10/195,505, the contents of which being incorporated by reference. Similarly, the property is very important for the present invention—in order to obtain sufficient spatial resolution.

For further details regarding different kind of detectors for use in the present invention, reference is made to the following U.S. Patents by Tom Francke et al. and assigned to XCounter AB of Sweden, which patents are hereby incorporated by reference: U.S. Pat. Nos. 6,118,125; 6,373,065; 6,337,482; 6,385,282; 6,414,317; 6,476,397; 6,477,223; 6,518,578; 6,522,722; 6,546,070; 6,556,650; 6,600,804; and 6,627,897.

Alternative detectors to be used in the present invention include other kinds of direction sensitive detectors, e.g. silicon PIN-diodes with edge-on incidence of radiation.

The individual conductive anode/readout elements 27 of a detector are arranged side by side in a row orthogonal to the xz-plane and define a respective angle $\beta_1, \ldots, \beta_M$ with respect to the xz-plane so that all the anode/readout elements 27 point towards a single point of the interaction trajectory 2b of the radiation beam 2a with the object 5, and detect therefore different angular portions $\beta_1, \ldots, \beta_M$ of the fan-shaped ray bundle entered into the line detector.

The line detectors $6a_1$–$6a_{n-1}$, $6a_{n+1}$–$6a_N$ are thus capable to simultaneously record coherent scatter imaging data sufficient to form a plurality of one-dimensional images, each being composed of radiation as coherently scattered in the examination object 5 in a respective angle $\beta_1, \ldots, \beta_M$—one signal from each of the line detectors $6a_1$–$6a_{n-1}$, $6a_{n+1}$–$6a_N$ is needed to form each of the plurality of one-dimensional images.

The radiation detector arrangement 6 of the apparatus of FIG. 1 comprises also a detector $6a_n$ arranged in the path of the radiation beam 2a to measure the transmission through the examination object 5 simultaneously with the simultaneous recording of the coherent scatter imaging data. The detector $6a_n$ may be a point detector or may be a detector of the kind as described with reference to FIGS. 2a–b to not only measure the transmission by an anode/readout element arranged with a β-angle (i.e. an angle with respect to the xz-plane) of 0°, but also radiation photons coherently scattered in the yz-plane.

Still further, the device 7 is provided for moving the radiation source 1, the collimator 4, and the radiation detector arrangement 6 relative the object 5 in a direction in the xy-plane (i.e. in a plane orthogonal to the axis of symmetry 3), while the individual line detectors $6a_1$–$6a_{n-1}$, $6a_{n+1}$–$6a_N$ together record a plurality of line images of radiation as coherently scattered in the object 5 in the angles $\beta_1, \ldots, \beta_M$ to thereby produce coherent scatter imaging data sufficient to form a plurality of two-dimensional images, each being composed of radiation as coherently scattered in the object 5 in a respective one of the angles $\beta_1, \ldots, \beta_M$. A line image of the radiation as transmitted through the object is obtained concurrently by the detector $6a_n$.

The device 7 may additionally be adapted to move the divergent radiation source 1 and the radiation detector arrangement 6 relative the object 5 in second direction in the xy-plane, while the line detectors $6a_1$–$6a_{n-1}$, $6a_{n+1}$–$6a_N$ together record a plurality of line images of radiation as scattered in the object 5 in the angles $\beta_1, \ldots, \beta_M$ to thereby produce coherent scatter imaging data sufficient to form a plurality of three-dimensional images, each being composed of radiation as coherently scattered in the object 5 in a respective one of the angles $\beta_1, \ldots, \beta_M$. A two-dimensional image of the radiation as transmitted through the object is obtained concurrently by the detector $6a_n$.

Figure 3A:
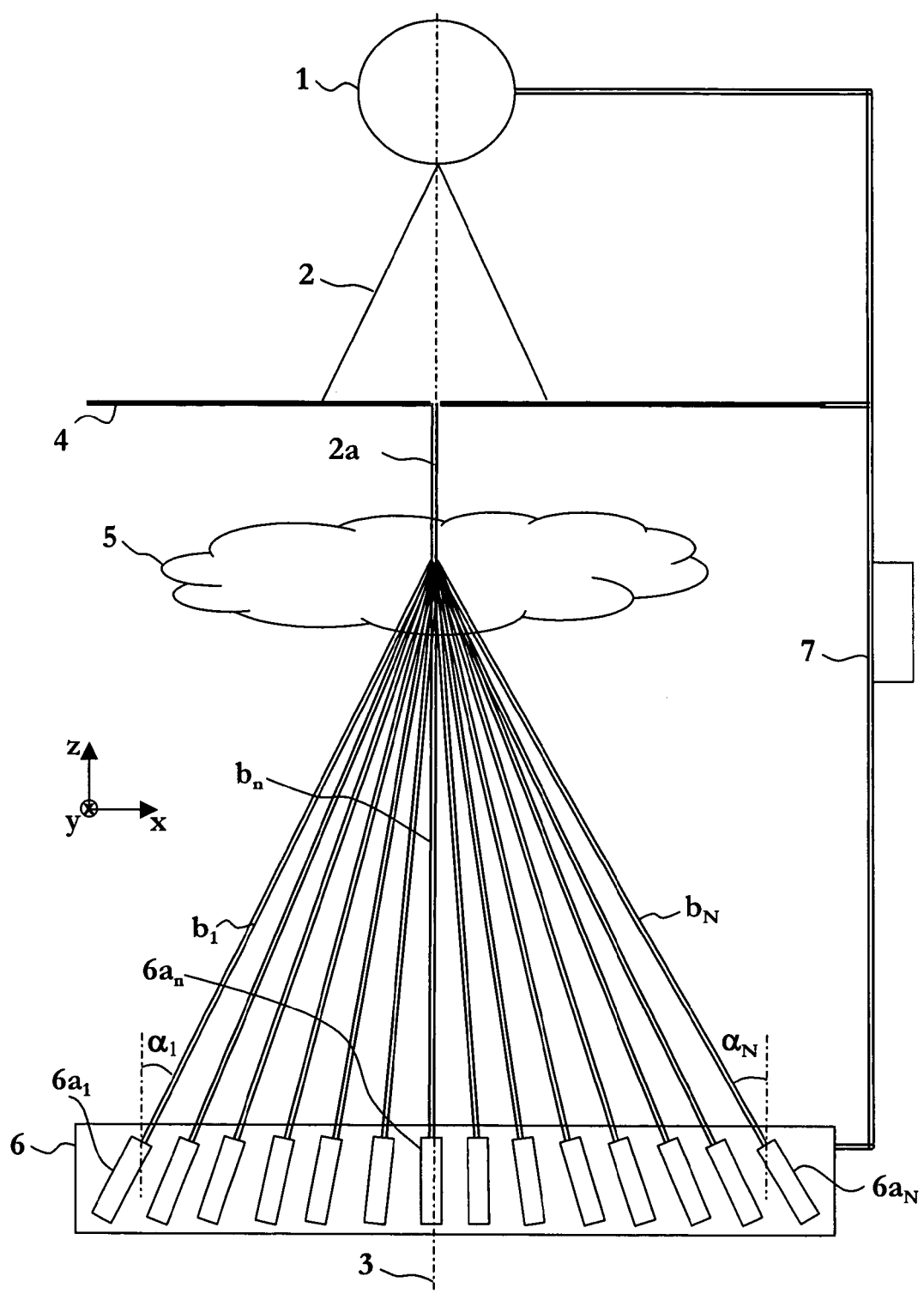
FIG. 3a illustrates schematically, in a side view, an apparatus for obtaining coherent scatter imaging data for x-ray examination of an object according to a further preferred embodiment of the present invention.
Figure 3B:
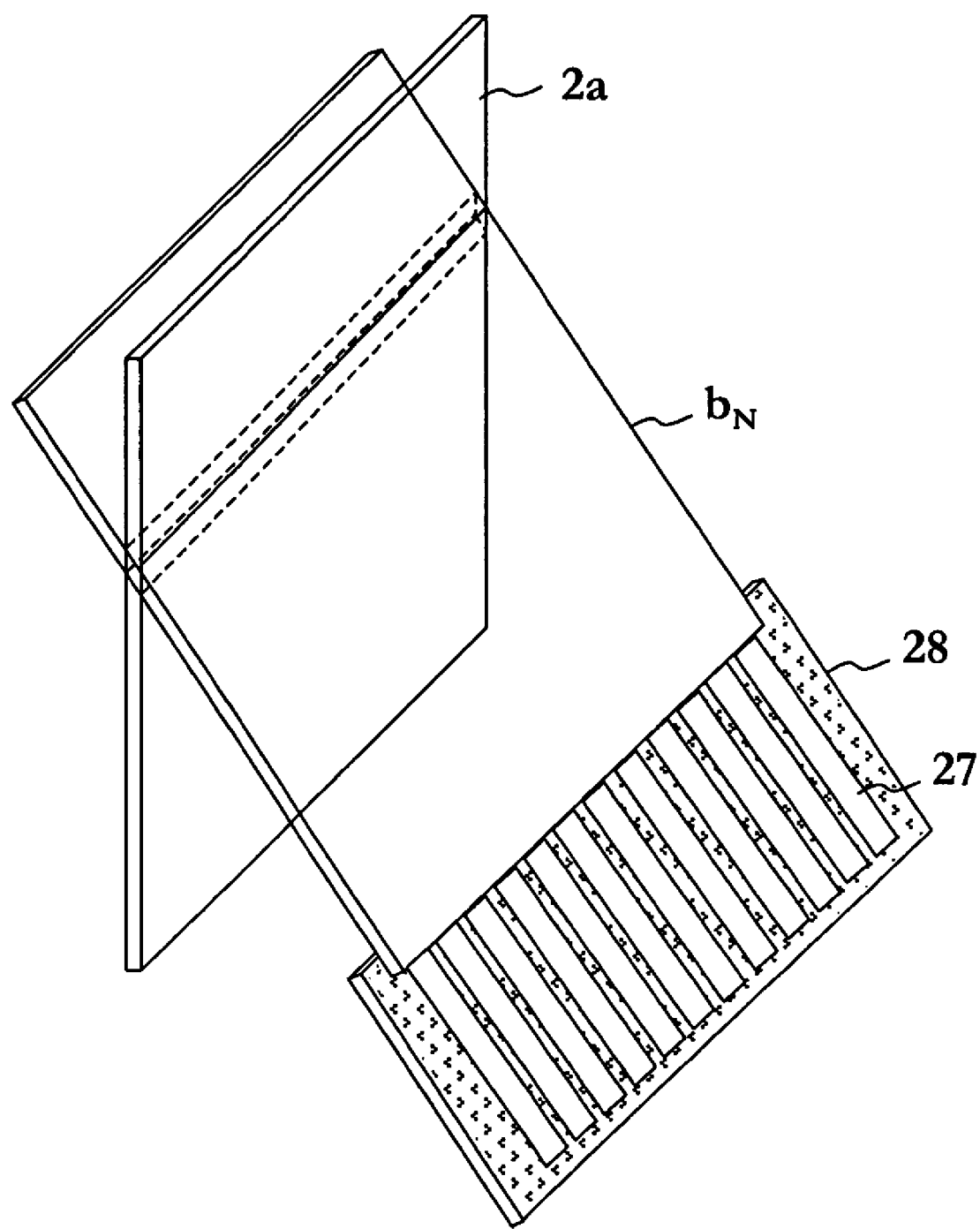
FIG. 3b illustrates schematically, in a perspective view, portions of the apparatus of FIG. 3b.

Turning now to FIGS. 3a–b, a second preferred embodiment of the present invention will be described. The collimator 4 comprises here a slit shaped opening, where the slit extends in the y-direction and as a consequence, the radiation beam 2a is substantially sheet-shaped. The openings of the line detectors $6a_1$–$6a_{n-1}$, $6a_{n+1}$–$6a_N$ are parallel with the substantially sheet-shaped radiation beam 2a, and the line detectors $6a_1$–$6a_{n-1}$, $6a_{n+1}$–$6a_N$ are directed towards the same small portion of the trajectory 2b of the radiation beam 2a in the examination object 5, and the detector elements 27 of each of the line detectors $6a_1$–$6a_{n-1}$, $6a_{n+1}$–$6a_N$ are separated, elongated and arranged to provide coherent scatter imaging data sufficient to form one of a plurality of one-dimensional images.

However, actions have to be taken to reduce scattered radiation in the plane of the detector, otherwise the images will be blurred. One solution is to arrange the detector arrangement 6 very far from the object 5. Alternatively, or additionally, the detectors $6a_1$–$6a_{n-1}$, $6a_{n+1}$–$6a_N$ may be made very long in the direction of the incident radiation to be detected, the anode/readout elements 27 may be arranged in the far end only of the detectors, the detectors may be provided with anti-scatter grids in their front ends, and/or radiation absorbing interstitial barriers may be provided in between each of the anode/readout elements 27 to prevent unwanted scattered radiation in the plane of the detector from crossing several of the anode/readout elements 27, and to consequently blur the image recorded.

The line detectors $6a_1$–$6a_{n-1}$, $6a_{n+1}$–$6a_N$ define different angles $\alpha_1$–$\alpha_{n-1}$, $\alpha_{n+1}$–$\alpha_N$ with respect to the axis of symmetry 3 in the xz-plane (i.e. the plane in which the axis of symmetry 3 and the stack of line detectors are).

The radiation detector arrangement 6 may like in previous embodiment comprise a detector $6a_n$ arranged in the path of the radiation beam 2a to measure the transmission through the examination object 5 simultaneously with the simultaneous recording of the coherent scatter imaging data. Preferably, the detector $6a_n$ is a line detector similar to the other line detectors described in this description, which line detector $6a_n$ performs instantaneous one-dimensional imaging of the cross section of the substantially sheet-shaped radiation beam $2a$.

The apparatus of FIG. 3a may further comprise the device 7 for moving the radiation detector arrangement 6 and optionally the radiation source 1 relative the object 5, while the line detectors $6a_1$–$6a_{n-1}$, $6a_{n+1}$–$6a_N$ together record a plurality of line images of radiation as scattered in the object 5 in a plurality of different angles $\alpha_1$–$\alpha_{n-1}$, $\alpha_{n+1}$–$\alpha_N$ to thereby produce coherent scatter imaging data sufficient to form a plurality of images, each being composed of radiation as coherently scattered in the examination object in a respective angle $\alpha_1$–$\alpha_{n-1}$, $\alpha_{n+1}$–$\alpha_N$. The device may move the radiation source 1 and the radiation detector arrangement 6 relative the object 5 in any direction in the xz-plane. If scanning is performed in two different directions three-dimensional coherent scatter imaging data can be produced. A two- or even three-dimensional image of the radiation as transmitted through the object is obtained concurrently by the detector $6a_n$.

In summary, by the FIGS. 1–2 embodiment one-dimensional images of coherently scattered radiation in the examination object is obtained instantaneously in the z-direction. The number of pixels in each one-dimensional image is N–1, the number of images is M, and they are produced from radiation scattered off the radiation beam both in the yz- and xz-planes. Simultaneous point measurement of transmission is obtained. Scanning is performed in the xy-plane. By the FIG. 3 embodiment one-dimensional images of coherently scattered radiation in the examination object is obtained instantaneously in the y-direction. The number of pixels in each one-dimensional image is M, the number of images is N–1, and they are produced from radiation scattered off the radiation beam in the xz-plane. Simultaneous one-dimensional measurement of transmission is obtained. Scanning is performed in the xz-plane.

What is claimed is:

1. An apparatus for simultaneously obtaining plurality of one-dimensional images of an examination object, wherein different ones of said one-dimensional images are formed from radiation coherently scattered at different angles, said apparatus comprising:

a radiation source arrangement for creating a collimated radiation beam of ionizing radiation for irradiating said examination object; and a radiation detector arrangement comprising a stack of line detector units, each line detector unit being directed towards a small portion of a trajectory of said radiation beam in said examination object to allow a respective ray bundle of said radiation beam as coherently scattered in said examination object to enter the line detector unit and be detected therein; wherein each of said line detector units has an elongated opening extending essentially orthogonal to said radiation beam for entry of the respective coherently scattered ray bundle; a row of individual detector elements arranged essentially parallel with said elongated opening for detecting different portions of said ray bundle scattered at different angles with respect to a plane whose normal is parallel with the extension of the elongated opening; and is of the kind wherein charges or photons, generated by interactions between the respective coherently scattered ray bundle and a detection medium within the respective line detector unit and traveling in a direction essentially perpendicular to the respective coherently scattered ray bundle, are detected by said row of individual detector elements;

said line detector units are direction sensitive and directed towards different adjacent positions along the trajectory of said radiation beam in said examination object so that ray bundles of said radiation beam as coherently scattered in different small portions of said examination object enter different ones of said line detector units and are detected therein; and said radiation detector arrangement is adapted to form each one of said plurality of one-dimensional images from each of said line detector units detected by an individual detector element thereof, wherein the individual detector elements, which detect the signals used for the formation of a single one-dimensional image, detect portions of the ray bundles that are scattered at a similar angle, wherein said plurality of one-dimensional images are images along the radiation beam as detected at different angles with respect to said plane.

2. The apparatus of claim 1 wherein the row of individual detector elements of each of said line detector units is essentially orthogonal to a plane, in which an axis of symmetry and said stack of line detector units are located; and the individual detector elements of each of said line detector units are separated, elongated, and directed so their extension lines converge in a respective point in said different small portions, and therefore detect different angular portions of the coherently scattered ray bundle entered into the respective line detector unit so that the signal from each of said line detector units is needed to form each of said plurality of one-dimensional images.

3. The apparatus of claim 1 wherein said line detector units are directed towards different positions along the trajectory of said radiation beam in said examination object, which directions define angles with respect to an axis of symmetry in said plane, in which said axis of symmetry and said stack of line detector units are located, which angles have the same magnitude.

4. The apparatus of claim 1 wherein said radiation detector arrangement comprises a detector unit arranged in a path of said radiation beam to measure transmission through said examination object simultaneously with simultaneous recording of coherent scatter imaging data.

5. The apparatus of claim 1 wherein each of said line detector units is a gaseous-based parallel plate detector.

6. The apparatus of claim 5 wherein each of said line detector units is an avalanche amplification detector.

7. The apparatus of claim 1 further comprising a device for moving said radiation source arrangement and said radiation detector arrangement relative to said examination object in a direction in a plane orthogonal to an axis of symmetry, while said line detector units are together adapted to record a plurality of line images of radiation as scattered in said examination object at a plurality of different angles to thereby produce coherent scatter imaging data sufficient to form a plurality of two-dimensional images, each being composed from radiation as coherently scattered in said examination object at a respective angle.

8. The apparatus of claim 1 further comprising a device for moving said radiation source arrangement and said radiation detector arrangement relative to said examination object in two different directions in said plane orthogonal to an axis of symmetry, while said line detector units are together adapted to record a plurality of line images of radiation as scattered in said examination object at a plurality of different angles to thereby produce coherent scatter imaging data sufficient to form a plurality of three-dimensional images, each being composed from radiation as coherently scattered in said examination object at a respective angle.

9. An apparatus for simultaneously obtaining a plurality of one-dimensional images of an examination object, wherein different ones of said one-dimensional images are formed from radiation coherently scattered at different angles, said apparatus comprising:
a radiation source arrangement for creating a radiation beam of ionizing radiation having an essentially line-shaped cross section, extending in a first direction, said radiation beam being provided for irradiating said examination object;
a radiation detector arrangement comprising line detector units arranged in a stack extending in a second direction substantially orthogonal to said first direction and to said radiation beam, all of said line detector units being direction sensitive and directed towards a single small portion of a trajectory of said radiation beam in said examination object to allow ray bundles of said radiation beam as coherently scattered in said examination object at different angles with respect to a plane whose normal is essentially parallel with said second direction to enter different ones of said line detector units and be detected therein; wherein
each of said line detector units has an elongated opening extending essentially parallel with said first direction for entry of the respective coherently scattered ray bundle; a row of individual detector elements arranged essentially parallel with said elongated opening; and is of the kind wherein charges or photons, generated by interactions between the respective coherently scattered ray bundle and a detection medium within the respective line detector unit and traveling in a direction essentially perpendicular to the respective coherently scattered ray bundle, are detected by said row of individual detector elements and;
said line detector units are directed towards the same small portion of the trajectory of said radiation beam in said examination object; and
said radiation detector arrangement is adapted to form each one of said plurality of one-dimensional images from signals from a single line detector unit as detected by the individual detector elements thereof, wherein said plurality of one-dimensional images are images along said first direction as detected at different angles with respect to said plane.

10. The apparatus of claim 9 wherein said line detector units are directed towards the same small portion of the trajectory of said radiation beam in said examination object; which directions define different angles with respect to an axis of symmetry in said plane, in which said axis of symmetry and the stack of line detector units are located.

11. The apparatus of claim 9 wherein said radiation detector arrangement comprises a detector unit arranged in the path of said radiation beam to measure transmission through said examination object simultaneously with simultaneous recording of coherent scatter imaging data.

12. The apparatus of claim 9 wherein each of said line detector units is a gaseous-based parallel plate detector.

13. The apparatus of claim 12 wherein each of said line detector units is an avalanche amplification detector.

14. The apparatus of claim 9 further comprising a device for moving said radiation detector arrangement and said radiation source arrangement relative to said examination object, while said line detector units are together adapted to record a plurality of line images of radiation as scattered in said examination object at a plurality of different angles to thereby produce coherent scatter imaging data sufficient to form a plurality of images, each being composed from radiation as coherently scattered in said examination object at a respective angle.

15. A method for simultaneously obtaining plurality of one-dimensional images of an examination object, wherein different ones of said one-dimensional images are formed from radiation coherently scattered at different angles, said method comprising the steps of:
directing a collimated radiation beam of ionizing radiation towards said examination object; and
directing each one of a plurality of line detector units arranged in a stack towards a small portion of a trajectory of said radiation beam in said examination object to allow a respective ray bundle of said radiation beam as coherently scattered in said examination object to enter the line detector unit; and
detecting said ray bundles entered into said line detector units, wherein
each of said line detector units has an elongated opening extending essentially orthogonal to said radiation beam for entry of the respective coherently scattered ray bundle; a row of individual detector elements arranged essentially parallel with said elongated opening for detecting different portions of said ray bundle scattered at different angles with respect to a plane whose normal is parallel with the extension of the elongated opening; and is of the kind wherein charges or photons, generated by interactions between the respective coherently scattered ray bundle and a detection medium within the line detector unit and traveling in a direction essentially perpendicular to the respective coherently scattered ray bundle, are detected by said row of individual detector elements;
said line detector units are direction sensitive and directed towards different adjacent positions along the trajectory of said radiation beam in said examination object so that ray bundles of said radiation beam as coherently scattered in different small portions of said examination object enter different ones of said line detector units and are detected therein; and
each one of said plurality of one-dimensional images are formed from a signal from each of said line detector units as detected by an individual detector element thereof, wherein the individual detector elements, which detect the signals used for the formation of a single one-dimensional image, detect portions of the ray bundles that are scattered at a similar angle, wherein said plurality of one-dimensional images are images along the radiation beam as detected at different angles with respect to said plane.

16. A method for simultaneously obtaining a plurality of one-dimensional images of an examination object, wherein different ones of said one-dimensional images are formed from radiation coherently scattered at different angles, said method comprising the steps of:
directing a radiation beam of ionizing radiation having an essentially line-shaped cross section extending in a first direction towards said examination object; and
directing a plurality of direction sensitive line detector units arranged in a stack, which extends in a second direction substantially orthogonal to said first direction and to said radiation beam, towards a single small portion of a trajectory of said radiation beam in said examination object to allow ray bundles of said radiation beam as coherently scattered in said examination object at different angles with respect to a plane whose normal is essentially parallel with said second direction to enter different ones of said line detector units; and separately detecting said ray bundles entered into said line detector units, wherein each of said line detector units has an elongated opening extending essentially parallel with said first direction for entry of the respective coherently scattered ray bundle; a row of individual detector elements arranged essentially parallel with said elongated opening; and is of the kind wherein charges or photons, generated by interactions between the respective coherently scattered ray bundle and a detection medium within the respective line detector unit and traveling in a direction essentially perpendicular to the respective coherently scattered ray bundle, are detected by said row of individual detector elements;

said line detector units are directed towards said radiation beam in said examination object; and each one of said plurality of one-dimensional images is formed from signals from a single line detector unit as detected by the individual detector elements thereof, wherein said plurality of one-dimensional images are images along said first direction as detected at different angles with respect to said plane.

* * * * *